(12) United States Patent
Kandimalla et al.

(10) Patent No.: US 6,372,427 B1
(45) Date of Patent: *Apr. 16, 2002

(54) COOPERATIVE OLIGONUCLEOTIDES

(75) Inventors: Ekambar R. Kandimalla, Worcester; Sudhir Agrawal, Shrewsbury, both of MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/420,672

(22) Filed: Apr. 12, 1995

(51) Int. Cl.$^7$ .................. C12Q 1/68; C07H 21/04; C12N 15/85
(52) U.S. Cl. .................. 435/6; 435/91.1; 435/325; 435/375; 536/23.1; 536/24.5
(58) Field of Search .................. 536/23.1, 24.5, 536/25.3; 514/44; 436/94, 6; 435/325, 375, 91.1

(56) References Cited

U.S. PATENT DOCUMENTS 5,166,195 A * 11/1992 Ecker .................. 514/44

FOREIGN PATENT DOCUMENTS

| EP | 0 185 494 | 6/1986 |
|---|---|---|
| GB | 2 225 112 A | 5/1990 |
| WO | WO 91/06626 | 5/1991 |
| WO | WO 94/17086 | 8/1994 |
| WO | WO 94/23028 | 10/1994 |
| WO | WO 95/01985 | 1/1995 |

OTHER PUBLICATIONS

Distefano et al., Cooperative binding of oligonucleotides to DNA by triple helix formation: dimerization via Watson-Crick hydrogen bonds, J. Am. Chem. Soc., vol. 13, pp. 5901–5902, 1991.*
Rojanasakul, Antisense oligonucleotide therapeutics: drug delivery and targeting, Advanced Drug Delivery Reviews, vol. 18, pp. 115–131, 1996.*
Miller et al., Gene transfer and antisense nucleic acid techniques, Parasitology Today, vol. 10(3), pp. 92–97, 1994.*
Gura, Antisense has growing pains, Science, vol. 270, pp. 575–577, Oct. 1995.*
Wu–Pong, Oligonucleotides: opportunties for drug therapy and research, Pharmaceutical Technology, vol. 18, pp. 102–114, Oct. 1994.*
Stull et al, Antigene, ribozyme, and aptamer nucleic acid drugs: progress and prospects, Pharmaceutical Research, vol. 12(4), pp. 465–483, 1995.*
Wagner, Gene inhibition using antisense oligonucleotides, Nature, vol. 372, pp. 333–335, Nov. 1994.*

Stein et al., Antisense oligonucleotides as therapeutic agents–Is the bullet realy magical?, Science, vol. 261, pp. 1004–1012, Aug. 1993.*
Weiss, Upping the antisense ante, Science News, vol. 139, pp. 108–109, 1991.*
Helene, The antigene strategy: control of gene expression by triplex forming oligonucleotides, Anti–Cancer Drug Design, vol. 6, pp. 569–584, 1991.*
Tazawa et al. (1972) *J. Mol. Biol.* 66:115–130.
Springgate et al. (1973) *Biopolymers* 12:2241–2260.
Stephenson et al. (1978) *Proc. Natl. Acad. Sci. (USA)* 75:285–288.
Asseline et al. (1984) *Proc. Natl. Acad. Sci. (USA)* 81:3297–3301.
Ptashne (1986) *A Genetic Switch*; Blackwell Scientific Publications and Cell Press: Palo Alto, CA.
Maher III et al. (1987) *Arch. Biochem. Biophy.* 253:214–220.
Strobel et al. (1989) *J. Am. Chem. Soc.* 111:7286–7287.
Distefano et al. (1991) *J. Am. Chem. Soc.* 113:5901–5902.
Rao et al. (1991) *J. Org. Chem.* 56:786–797.
Agrawal et al. (1992) *Antisense Res. Dev.* 2:261.
Distefano et al. (1992) *J. Am. Chem. Soc.* 114:11006–11007.
Woolf et al. (1992) *Proc. Natl. Acad. Sci. (USA)* 89:7305–7309.
Bayever et al. (1993) *Antisense Res. Dev.* 3:383–390.
Colocci et al. (1993) *J. Am. Chem. Soc.* 115:4468–4473.
Cornish et al. (1993) *Pharmacol. Commun.* 3:239–247.
Gryaznov et al. (1993) *Nucl. Acids Res.* 21:5909–5915.
Lilley et al. (1993) *Quarterly Rev. Biophys.* 26:131–175.
Methods Mol. Biol. (1993) vol. 20, (Agrawal, ed.) Humana Press, Totowa, NJ.
Stein et al. (1993) *Science* 261:1004–1012.
Colocci et al. (1994) *J. Am. Chem. Soc.* 116:785–786.
Galbraith et al. (1994) *Antisense Res. Dev.* 4:201–207.
Padmapriya et al. (1994) *Antisense Res. Dev.* 4:185–199.

* cited by examiner

Primary Examiner—Andrew Wang
(74) Attorney, Agent, or Firm—Hale and Dorr LLP

(57) ABSTRACT

Disclosed is a composition comprising at least two synthetic, cooperative oligonucleotides, each comprising a region complementary to one of tandem, non-overlapping regions of a target single-stranded nucleic acid, and each further comprising a dimerization domain at a terminus of each of the oligonucleotides, the dimerization domains of the oligonucleotides being complementary to each other. Also disclosed are duplex structures, ternary complexes, pharmaceutical formulations, and methods utilizing the cooperative oligonucleotides of the invention.

22 Claims, 10 Drawing Sheets

COOPERATIVE OLIGONUCLEOTIDES

BACKGROUND OF THE INVENTION

Progress in chemical synthesis of nuclease resistant oligonucleotides (*Methods Mol. Biol.* (1993) Vol. 20, (Agrawal, ed.) Humana Press, Totowa, N.J.) and developments in large scale solid phase synthesis of oligonucleotides (Agrawal, ed.) *Methods Mol. Biol.* (1993) Vol. 20, Humana Press, Totowa, N.J.); Padmapriya et al. (1994) *Antisense Res. Dev.* 4:185–199) has permitted antisense oligonucleotides to advance to human clinical trials (Bayever et al. (1993) *Antisense Res. Dev.* 3:383–390). In principle, antisense oligonucleotides utilize highly sequence-specific complementary nucleo-base recognition of target nucleic acids through Watson-Crick hydrogen bonding between A and T, and G and C, that leads to the development of less toxic and more site specific chemotherapeutic agents (Stephenson et al. (1978) *Proc. Natl. Acad. Sci. (USA)* 75:285–288). As per theoretical calculations, an oligonucleotide of 13 or more bases long should bind to a unique sequence that occurs only once in a eucaryotic mRNA pool.

Contrary to the popular belief, it was recently shown that the increase in the length of an antisense oligonucleotide beyond the minimum length that can hybridize to the target (i.e. 11–14 bases) decreases its specificity rather than increasing (Woolf et al. (1992) *Proc. Natl. Acad. Sci. (USA)* 89:7305–7309). Potentially, this decrease in hybridization specificity would lead to non-sequence-specific target binding and subsequent increased toxicity (Stein et al. (1993) *Science* 261:1004–1012).

Thus, what is needed are improved antisense oligonucleotides optimized for therapeutic and diagnostic use which have improved affinity, specificity, and biological activity, and little or no toxicity.

SUMMARY OF THE INVENTION

The present invention provides cooperative oligonucleotides with improved sequence specificity for a single-stranded target, reduced toxicity, and improved biological activity as antisense molecules.

Surprisingly, it has been discovered that two short oligonucleotides (25 nucleotides or less) bind to adjacent sites on the target nucleic acid in a cooperative manner, allowing for an interaction with greater sequence specificity than can a single longer oligonucleotide having a length equal to the two shorter oligonucleotides.

Accordingly, in a first aspect, the present invention provides a composition including at least two synthetic cooperative oligonucleotides, each comprising a region complementary to one of tandem, non-overlapping regions of a target single-stranded nucleic acid, and a dimerization domain at a terminus of each of the oligonucleotides. The dimerization domains of the cooperative oligonucleotides are complementary to each other, and the target nucleic acid being an mRNA, single-stranded viral DNA, or single-stranded viral RNA.

In some preferred embodiments, the oligonucleotides each are complementary to tandem regions of the target nucleic acid that are separated by 0 to 3 bases. In some preferred embodiments, each of the oligonucleotides are about 9 to 25 nucleotides in length.

In one embodiment, the composition consists of two cooperative oligonucleotides, the dimerization domain of a first or one of the oligonucleotides being located at its 3' terminal portion, and being complementary to the dimerization domain of a second or the other oligonucleotide which is located at its 5' terminal portion. Alternatively, the dimerization domain of the first cooperative oligonucleotide is located at its 3' terminal portion, and is complementary to the dimerization domain of a second oligonucleotide which is located at its 3' terminal portion. Alternatively, the dimerization domain of the first cooperative oligonucleotide is located at its 5' terminal portion, and is complementary to a dimerization domain of the second oligonucleotide which is located at its 5' terminal portion.

The invention provides in another aspect a duplex structure comprising first and second synthetic cooperative oligonucleotides, each oligonucleotide comprising a region complementary to the non-overlapping, tandem regions of the target nucleic acid which is an mRNA, single-stranded viral RNA, or single-stranded viral DNA. The first oligonucleotide in the duplex has a terminal dimerization domain complementary and hybridized to the dimerization domain of the second oligonucleotide. In some embodiments, each of the oligonucleotides are about 9 to 25 nucleotides in length, and in others, the dimerization domains of the first and second oligonucleotides each comprise about 3 to 7 nucleotides. In some embodiments, the invention provides first and second oligonucleotides which are complementary to tandem regions of the target nucleic acid separated by 0 to 3 bases.

The invention also provides pharmaceutical formulations containing the compositions or duplex structures described above, and methods of inhibiting the expression of a nucleic acid in vitro comprising the step of treating the nucleic acid with the pharmaceutical formulations of the invention. In some embodiments, the first and second oligonucleotides are complementary to an HIV DNA or an HIV RNA.

In another aspect, the invention provides a ternary complex comprising the duplex structure of the invention and a target oligonucleotide to which regions of the first and second cooperative oligonucleotides are complementary. The target oligonucleotide is an mRNA, a single-stranded viral DNA, or a single-stranded DNA.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Cooperative interactions between biological macromolecules are important in nature. For example, the cooperative interactions between proteins and nucleic acids are vital for the regulation of gene expression. Cooperative interactions serve to improve sequence specificity, affinity, and biological activity (Ptashne (1986) *A Genetic Switch*; Blackwell Scientific Publications and Cell Press: Palo Alto, Calif.) Cooperative binding of drugs to DNA (Asseline et al. (1984) *Proc. Natl. Acad. Sci. (USA)* 81:3297–3301; Rao et al. (1991) *J. Org. Chem.* 56:786–797), of oligonucleotides or their conjugates to single stranded DNA (Tazawa et al. (1972) *J. Mol. Biol.* 66:115–130; Maher et al. (1988) *Nucl. Acids Res.* 16:3341–3358; Springgate et al. (1973) *Biopolymers* 12:2241–2260; and Gryaznov et al. (1993) *Nucl. Acids Res.* 21:5909–5915), of oligonucleotides to RNA (Maher III et al. (1987) *Arch. Biochem. Biophy.* 253:214–220), and of oligonucleotides to double-stranded DNA through triplex formation (Strobel et al. (1989) *J. Am. Chem. Soc.* 111:7286–7287; Distefano et al. (1991) *J. Am. Chem. Soc.* 113:5901–5902; Distefano et al. (1992) *J. Am. Chem. Soc.* 114:11006–11007; Colocci et al. (1993) *J. Am. Chem. Soc.* 115:4468–4473; Colocci et al. (1994) *J. Am. Chem. Soc.* 116:785–786) has been documented. Although these studies demonstrated the advantages of using cooperative interactions for small molecule-based drug development, there are no reports of optimizing the design of cooperative oligonucleotides for therapeutic uses.

The present invention provides synthetic oligonucleotides which interact with mRNA, single-stranded viral RNA, or single-stranded viral DNA ("target nucleic acids"), and have improved affinity, specificity, and biological activity as antisense molecules. At least two of the oligonucleotides of the invention are used to interact with a target nucleic acid, thereby enabling them to interact cooperatively, synergistically enhancing their ability (singly) to inhibit expression of the target nucleic acid.

The term "synthetic oligonucleotide" for purposes of this invention includes chemically synthesized polymers of about 7 to about 25, and preferably from about 9 to about 23 nucleotide monomers (nucleotide bases) connected together or linked by at least one 5' to 3' internucleotide linkage.

Figure 1A:
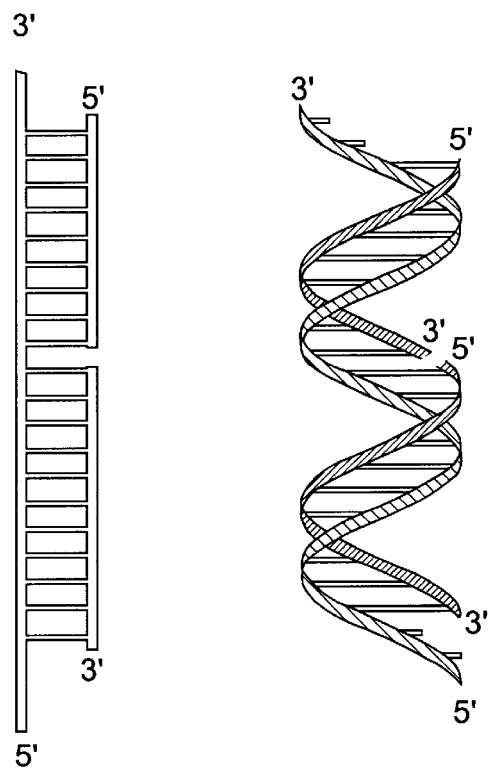
FIG. 1A is a schematic representation of the cooperative binding of two short oligonucleotides to tandem sites.
Figure 1B:
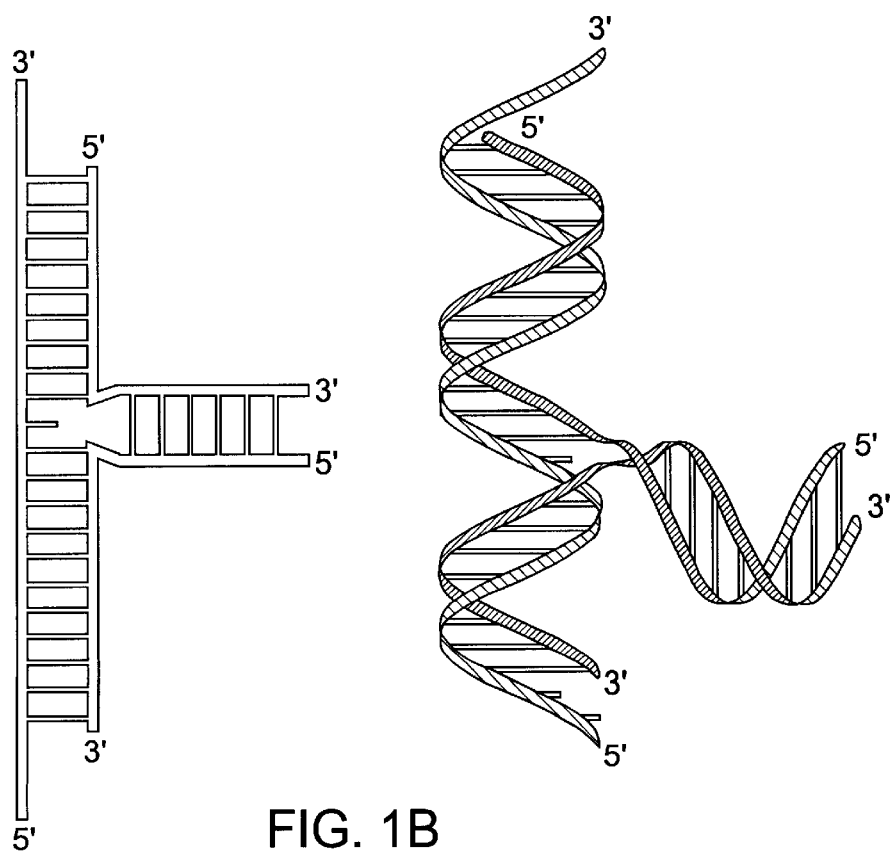
FIG. 1B is a schematic representation of the binding to adjacent sites on a target nucleic acid of cooperative oligonucleotides that have extended antisense dimerization domains and their dimerization.
Figure 1C:
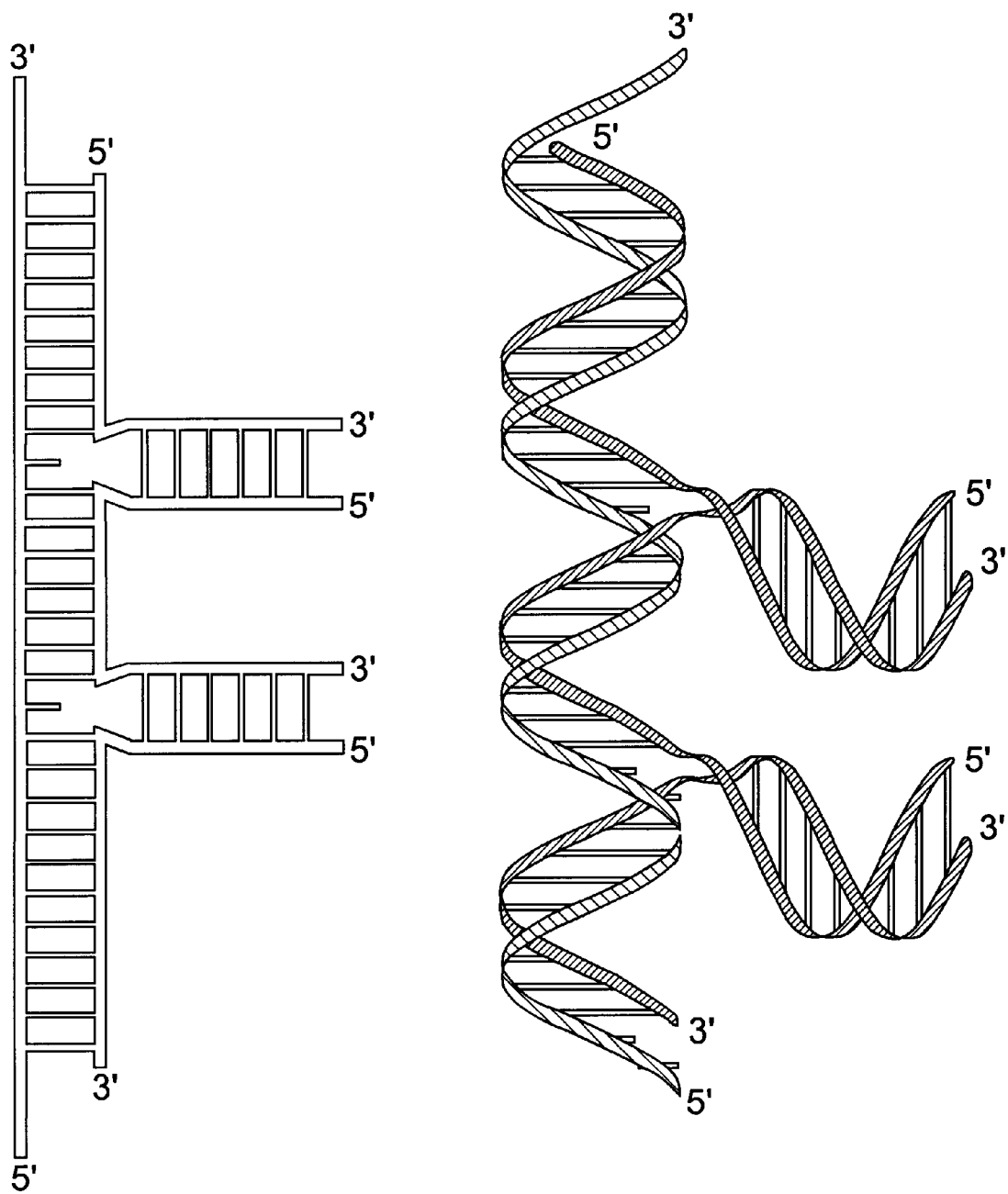
FIG. 1C is a schematic representation of the binding of three cooperative oligonucleotides of the invention to adjacent sites on a target nucleic acid.

Some cooperative oligonucleotides of the invention are complementary to non-overlapping, tandem regions of the target nucleic acid, as shown in FIG. 1A, while others are complementary to adjacent sites (FIGS. 1B and 1C). At least two of these oligonucleotides can used to control target nucleic acid expression.

For purposes of the invention, the term "oligonucleotide complementary to a target nucleic acid" is intended to mean an oligonucleotide sequence that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, pseudoknot formation. Such binding (by Watson-Crick base pairing) under physiological conditions is measured as a practical matter by observing interference with the function of the nucleic acid sequence.

The inhibitory ability of the cooperative oligonucleotides of the invention is enhanced even further when these oligonucleotides also include a terminal portion (i.e., a "dimerization domain") which is not complementary to the target nucleic acid, but rather which is complementary to each other, thereby enabling the formation of a dimers (FIG. 1B). The interaction of these cooperative oligonucleotides with the target nucleic acid leads to the formation of a more stable ternary complex as the result of dimerization of the complementary dimerization domains of these oligonucleotides. When the cooperative oligonucleotides of the invention have dimerization domains and hybridize together to form a duplex, the regions of the cooperative oligonucleotides which are complementary to the target nucleic acid may be separated by 0 to 3 bases.

The cooperative oligonucleotides of the invention may have any nucleotide sequence, as long as a portion of its sequence is complementary to a portion of a target nucleic acid, and, in the case of cooperative oligonucleotides which form duplexes with each other, as long as their terminal dimerization domains are not complementary to the target nucleic acid. These dimerization domains may be at the 3' termini of both cooperative oligonucleotides, at the 5' termini of both cooperative oligonucleotides, or at the 3' terminus of one cooperative oligonucleotide and the 5' terminus of the other cooperative oligonucleotide.

The cooperative oligonucleotides of the invention are composed of deoxyribonucleotides, ribonucleotides, or any combination thereof, with the 5' end of one nucleotide and the 3' end of another nucleotide being covalently linked, in some cases, via a phosphodiester internucleotide linkage. The oligonucleotides can be prepared by art recognized methods such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron. Lett.* 28:(31):3539–3542); Caruthers et al. (1987) *Meth. Enzymol.* 154:287–313; U.S. Pat. No. 5,149,798) which can be carried out manually or by an automated synthesizer and then processed (reviewed in Agrawal et al. (1992) *Trends Biotechnol.* 10:152–158).

The oligonucleotides of the invention may also be modified in a number of ways without compromising their ability to hybridize to nucleotide sequences contained within a targeted region of a particular gene.

The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups.

Preferable synthetic linkages include alkylphosphonates, phosphorothioates, phosphorodithioates, phosphate esters, alkylphosphonothioates, phosphoramidates, phosphoramidites, carbamates, carbonates, phosphate esters, acetamidate, and carboxymethyl esters. oligonucleotides with these linkages or other modifications can be prepared according to known methods (see, e.g., Agrawal and Goodchild (*Tetrahedron Lett.* (1987) 28:3539–3542); Agrawal et al. (*Proc. Natl. Acad. Sci.* (USA) (1988) 85:7079–7083) ; Uhlmann et al. *Chem. Rev.* (1990) 90:534–583; and Agrawal et al. (*Trends Biotechnol.* (1992) 10:152–158).

In one preferred embodiment of the invention, the oligonucleotide comprises at least one phosphorothioate linkage. Oligonucleotides with phosphorothioate linkages can be prepared using methods well known in the field such as methoxyphosphoramidite (see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

The term "modified oligonucleotide" also encompasses oligonucleotides with a modified base and/or sugar. Examples of such modified oligonucleotides include 2'-O-methyl or arabinose instead of ribose, or a 3',5'-substituted oligonucleotide having a sugar which, at both its 3' and 5' positions is attached to a chemical group other than a hydroxyl group (at its 3' position) and other than a phosphate group (at its 5' position). Such modified oligonucleotide may also be referred to as a capped species. In addition, unoxidized or partially oxidized oligonucleotides having a substitution in one nonbridging oxygen per nucleotide in the molecule are also considered to be modified oligonucleotides.

Such modifications can be at some or all of the internucleoside linkages, as well as at either or both ends of the oligonucleotide and/or in the interior of the molecule (reviewed in Agrawal et al. (1992) *Trends Biotechnol.* 10:152–158). Also considered as modified oligonucleotides are oligonucleotides having nuclease resistance-conferring bulky substituents at their 3' and/or 5' end(s) and/or various other structural modifications not found in vivo without human intervention. Other modifications include those which are internal or are at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position)

To demonstrate the cooperative nature of the oligonucleotides of the invention, oligonucleotides were prepared as described above and tested for their ability to inhibit the expression of a target gene.

The target chosen was a sequence in the initiation codon region of gag mRNA of HIV-1 (SEQ ID NOS:21 and 22) (Agrawal and Tang (1992) *Antisense Res. Dev.* 2:261). The list of oligonucleotides used in the study are shown in TABLE 1.

TABLE 1

| SEQ ID NO: | Sequence[a] (3' → 5') | Length (# bases) |
|---|---|---|
| 21 | CTAGAAGGAGAGAGATGGGTGCGAGAG | Target[b] |
| 22 | AGAAGGAGAGAGAUGGGUGCGAGAGCGUCAGUAUUAAGC | Target[b] |
| 1 | CCCACGCTC | 9 |
| 2 | TTCCTCTCTCTA | 12 |
| 3 | CTTCCTCTCTCT | 12 |
| 4 | TCTTCCTCTCTC | 12 |
| 5 | TTCCTCTCTCTACCCACGCTC | 21 |
| 6 | CTTCCTCTCTCT<u>G</u>CCCACGCTC | 22 |
| 7 | TCTTCCTCTCTC<u>CG</u>CCCACGCTC | 23 |
| 8 | CTTCCTCTCTCTA | 13 |
| 9 | TTCCTCTCTCTA<br>G<br>G<br>C | 15 |
| 10 | CTTCCTCTCTCT<br>G<br>G<br>C | 15 |
| 11 | CTTCCTCTCTCT<br>G<br>G<br>C<br>C | 16 |
| 12 | CTTCCTCTCTCT<br>G<br>G | 17 |

TABLE 1-continued

| SEQ ID NO: | Sequence[a] (3' → 5') | Length (# bases) |
|---|---|---|
| 13 |           C<br>          C<br>          G<br>CTTCCTCTCTCT<br>            G<br>            G<br>            C<br>            C<br>            G<br>            C<br>            G | 19 |
| 14 | CCCACGCTC<br>         C<br>         C<br>         G | 12 |
| 15 | CCCACGCTC<br>         C<br>         C<br>         G<br>         G | 13 |
| 16 | CCCACGCTC<br>         C<br>         C<br>         G<br>         G<br>         C | 14 |
| 17 | CCCACGCTC<br>         C<br>         C<br>         G<br>         G<br>         C<br>         G<br>         C | 16 |
| 18 | CCAC<u>T</u>CTC | 9 |
| 19 | CC<u>AA</u>C<u>T</u>CTC | 9 |
| 20 | TCTTCCTCTCTCTACCCACGCTCTC | 25 |
| 23 | TTCCTCTCTCTACCCAC<u>T</u>CTC | 21 |
| 24 | TTCCTCTCTCTACC<u>AA</u>C<u>T</u>CTC | 21 |

[a]underlined bases represent mismatches
[b]sequence is 5'→3'

Oligonucleotides 1 (SEQ ID NO:1) and 2 (SEQ NO:2) are designed to bind to 21 bases of the get nucleic acid at adjacent sites without any base gap between them (see FIG. 1A and TABLE 1). Thus, contact is expected to be maintained through the 3'-end of the oligonucleotide 1 and the 5'-end of the oligonucleotide 2 when these oligonucleotides bind to the target sequence at the adjacent sites. This results in cooperativity in the interactions of these two oligonucleotides. Oligonucleotides 3 (SEQ ID NO:3) and 4 (SEQ ID NO:4) bind to the same site as oligonucleotide 2 but are separated by 1 and 2 bases on the target sequence, gaps, respectively, from the binding site of oligonucleotide 1. Because of this gap these oligonucleotides are expected not to show any cooperativity in the binding of these oligonucleotide pairs to the target. Oligonucleotide 5 (SEQ ID NO:5) binds to the same 21 base target sequence on the target oligonucleotide that oligonucleotides 1 and 2 together bind. Oligonucleotide 6, a 22mer (SEQ ID NO:6) and oligonucleotide 7, a 23mer (SEQ ID NO:7) have 1 and 2 mismatches, respectively, in position that correspond to 1 and 2 base separation when oligonucleotides 1+3 and 1+4 bind to the target sequence together. Oligonucleotide 8 (SEQ ID NO:8) is a 13mer control oligonucleotide that binds to the same sequence as oligonucleotides 2 and 3 adjacent to oligonucleotide 1 without a base separation between them.

To further improve the cooperative interactions of the oligonucleotides binding to the target sequence at abutting sites, oligonucleotides 1 and 2 were both extended at the site of junction with complementary sequences so that they form a duplex stem upon interaction with the target, as shown in FIG. 1B. This extended antisense dimerization domain is designed not to have any complementarity with the adjacent bases of the antisense oligonucleotide binding site on the target. Oligonucleotides 9–17 (SEQ ID NOS:9–17) have an extended sequence on either the 5'- or 3'-end of the binding sequence, which forms a duplex stem between the two oligonucleotides when they bind to adjacent sites on the target (FIG. 1B). This extended antisense dimerization domain has no complementarity with the target sequence. Oligonucleotides 9 and 14 form a 3 base pair stem. Oligonucleotides 10 and 14 have the same length of extended antisense dimerization domain but with one base separating the two target sites of the binding oligonucleotide pair. Oligonucleotide pairs 11+15, 12+16, and 13+17 bind to the same length of the sequence on the target as oligonucleotide pair 10+14 but with 4, 5, and 7 base pair extended antisense dimerization domains, respectively.

Figure 2A:
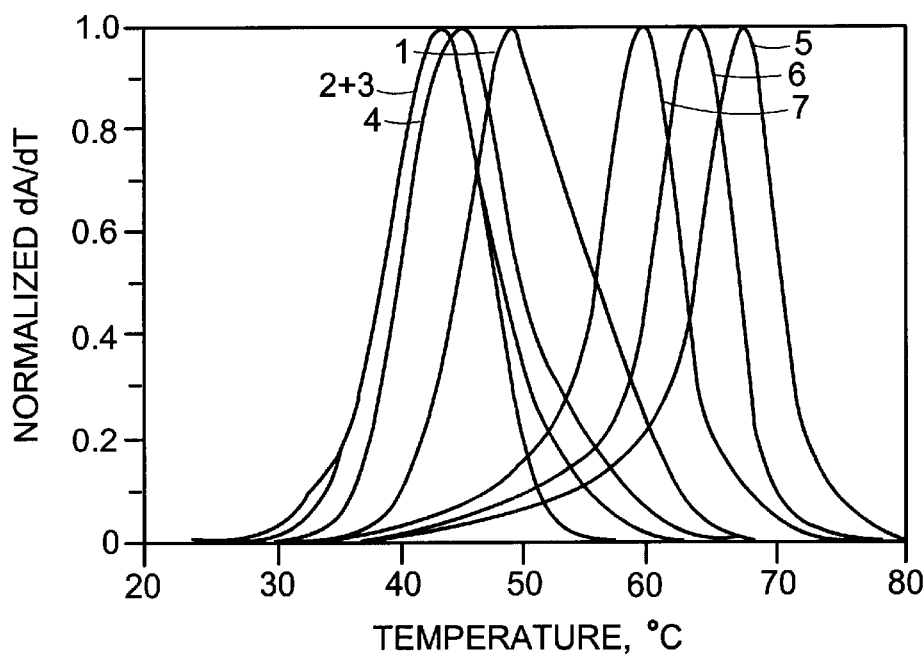
FIG. 2A is a graphic representation showing the thermal melting profile (dA/dT vs. T) of oligonucleotides 1–7 shown in FIG. 2 with their DNA target.

The initial evidence for cooperative binding of oligonucleotides 1 and 2 to their target sequence comes from thermal melting studies. TABLE 2 shows thermal melting data of the duplexes of these oligonucleotides individually and together with other corresponding oligonucleotides (FIG. 2). When oligonucleotides 1 and 2 bound side by side to the target, the resulting duplex has a Tm of 47.8° C.

Duplexes of oligonucleotides 1+3 and 1+4 with the target sequence have Tms of 44.4° C. and 460° C., respectively. The oligonucleotides 1 and 3 bind to the target with a 1 base gap between them, and the oligonucleotides 1 and 4 bind to the target with a 2 base gap between them. The Tm of the duplex formed by oligonucleotides 1 and 2 together with the target is more than the average of the duplexes formed by 1 and 2 individually with the target sequence (TABLE 2).

TABLE 2

| Oligos (SEQ ID NO:) | Complex[a,b] | Tm, ° C. |
|---|---|---|
| 1 | CTAGAAGGAGAGAGATGGGTGCGAGAG<br>                          CCCACGCTC | 49.1 |
| 2 | CTAGAAGGAGAGAGATGGGTGCGAGAG<br>         TTCCTCTCTCTA | 43.4 |
| 3 | CTAGAAGGAGAGAGATGGGTGCGAGAG<br>         CTTCCTCTCTCT | 43.6 |
| 4 | CTAGAAGGAGAGAGATGGGTGCGAGAG<br>         TCTTCCTCTCTC | 45.0 |
| 5 | CTAGAAGGAGAGAGATGGGTGCGAGAG<br>         TTCCTCTCTCTACCCACGCTC | 67.7 |
| 6 | CTAGAAGGAGAGAGATGGGTGCGAGAG<br>         CTTCCTCTCTCTG̲CCCACGCTC | 64.2 |
| 7 | CTAGAAGGAGAGAGATGGGTGCGAGAG<br>         TCTTCCTCTCTCC̲G̲CCCACGCTC | 59.9 |
| 1+2 | CTAGAAGGAGAGAGATGGGTGCGAGAG<br>         TTCCTCTCTCTACCCACGCTC | 47.8 |
| 1+3 | CTAGAAGGAGAGAGATGGGTGCGAGAG<br>         CTTCCTCTCTCT CCCACGCTC | 44.4 |
| 1+4 | CTAGAAGGAGAGAGATGGGTGCGAGAG<br>         TCTTCCTCTCTC CCCACGCTC | 45.9 |
| 1+8 | CTAGAAGGAGAGAGATGGGTGCGAGAG<br>         CTTCCTCTCTCTACCCACGCTC | 50.5 |

[a] = underlined bases represent mismatches
[b] = The target sequence, SEQ ID NO:21, is bolded and is 5' → 3'

Figure 2B:
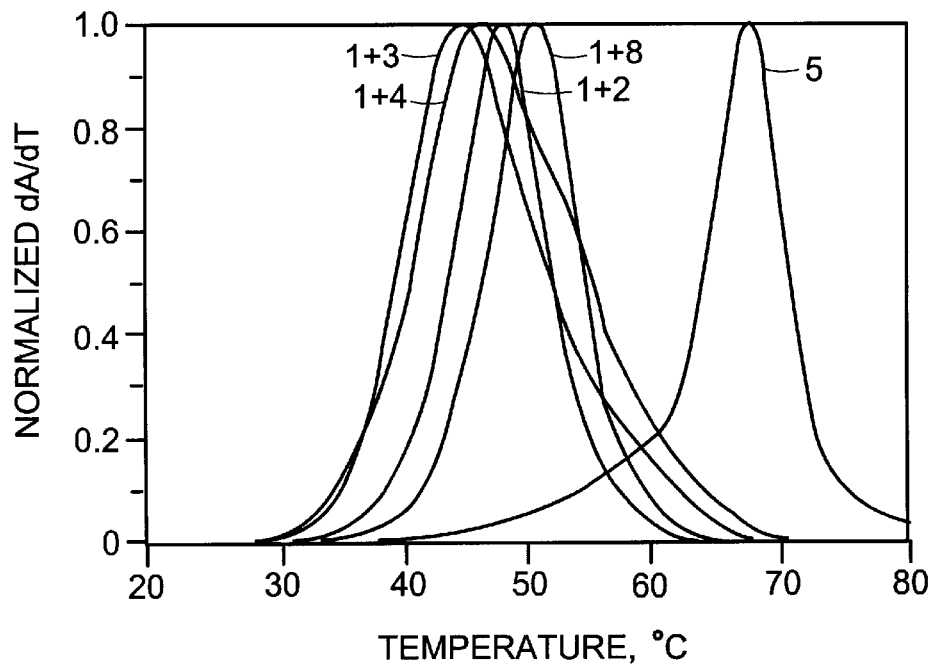
FIG. 2B is a graphic representation showing the thermal melting profile (dA/dT vs. T) of oligonucleotides 1+2, 1+3, 1+4, and 5 shown in FIG. 2 with their DNA target.

In contrast, in the latter two cases (1+3 and 1+4), the Tms are below the average of the two individual oligonucleotides in experiment. Further, in the case of the duplex formed with oligonucleotides 1+2 a sharp, single, cooperative transition was noticed (FIG. 2B). However, in the cases of the duplexes formed with 1+3 and 1+4, melting transitions were broad (FIG. 2B). This indicates that the two short oligonucleotides 1 and 2 targeted to two adjacent sites bind in a cooperative fashion, whereas those which bind leaving a one or two base gap between them do not interact cooperatively.

The duplex of oligonucleotide 5 which binds to the entire 21 base length has a Tm of 67.70° C. The duplex of oligonucleotide 6 (SEQ ID NO:6), a 22-mer with a mismatch in place that corresponds to one base gap between oligonucleotides 1 and 3, has a Tm of 64.2° C. Similarly, the duplex of oligonucleotide 7 (SEQ ID NO:7), a 23mer with two mismatches in a position that corresponds to the two base gap between oligonucleotides 1 and 4, has a Tm of 59.90° C. The lower melting temperatures of oligonucleotides 6 and 7 which bind to the target with one or two base mismatches indicate that these oligonucleotides can bind to a number of sites other than the perfectly matched target site at physiological temperatures. Thus, sequence specificity is decreasing.

Thermal melting studies of the duplexes of the oligonucleotides 9–17 demonstrates that the binding of these tandem oligonucleotides is further facilitated by the duplex stem (i.e., antisense dimerization domain) formed by extending the antisense dimerization domain. The stability of the ternary complex formed increases with an increase in the number of base pairs in the antisense dimerization domain, as shown in TABLE 3.

TABLE 3

| Oligos (SEQ ID NOS:) | Complex[a] | Tm, ° C. |
|---|---|---|
| 10 + 14 | CTAGAAGGAGAGAGATGGGTGCGAGAG<br>         CTTCCTCTCTCT CCCACGCTC<br>                                G C<br>                                G C<br>                                C G | 45.9 |
| 11 + 15 | CTAGAAGGAGAGAGATGGGTGCGAGAG<br>         CTTCCTCTCTCT CCCACGCTC<br>                                G C<br>                                G C<br>                                C G<br>                                C G | 47.3 |
| 12 + 16 | CTAGAAGGAGAGAGATGGGTGCGAGAG<br>         CTTCCTCTCTCT CCCACGCTC<br>                                G C<br>                                G C<br>                                C G<br>                                C G<br>                                G C | 48.4 |
| 13 + 1 | CTAGAAGGAGAGAGATGGGTGCGAGAG<br>         CTTCCTCTCTCT CCCACGCTC<br>                                G C<br>                                G C<br>                                C G<br>                                C G<br>                                G C<br>                                C G<br>                                G C | 53.2 |
| 9 + 14 | CTAGAAGGAGAGAGATGGGTGCGAGAG<br>         TTCCTCTCTCTACCCACGCTC<br>                                GC<br>                                GC<br>                                CG | 47.9 |

[a]Target, SEQ ID NO:21, is bolded and is 5' → 3'; complementary cooperative oligonucleotides are 3' → 5'

Figure 3:
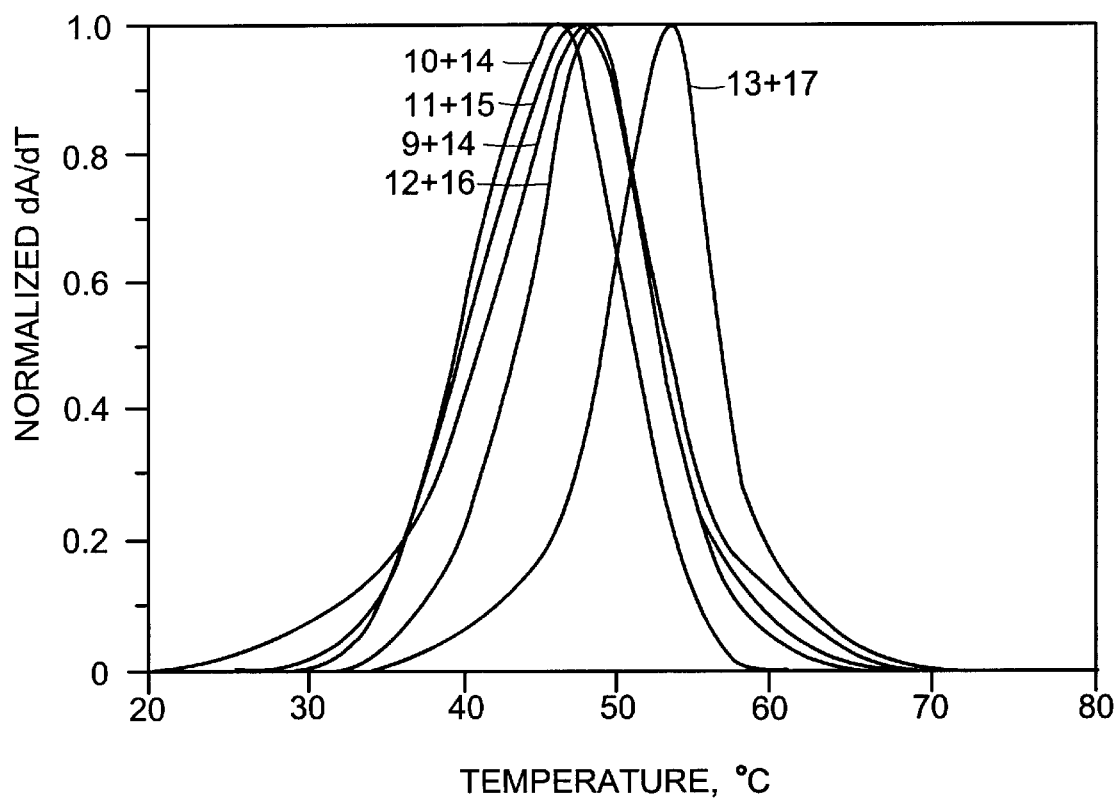
FIG. 3 is a graphic representation showing the thermal melting profiles (dA/dT vs. T) of the oligonucleotide combinations with extended antisense dimerization domains (10+14, 11+15, 9+14, 12+16, and 13+17)

For example, the double helical complexes with 3 base pair (oligonucleotides 10+14), 4 base pair (oligonucleotides 11+15), 5 base pair (oligonucleotides 12+16), and 7 base pair (oligonucleotides 13+17) antisense dimerization domains gave Tms of 45.9° C., 47.3° C., 48.4° C. and 53.2° C., respectively. Further increases in duplex stem length results in the formation of a stable complex between the two tandem oligonucleotides in the absence of the target sequence, an occurrence which is not desirable. In all the cases, a sharp cooperative single melting transition was observed (FIG. 3).

Modified cooperative oligonucleotides were studied for their antisense abilities. For example, phosphorothioate internucleotide-linked forms of cooperative oligonucleotides were studied for their ability to activate RNase H. RNase H is an enzyme that recognizes RNA-DNA heteroduplexes and hydrolyzes the RNA component of the heteroduplex (Cedergren et al. (1987) *Biochem. Cell Biol.* 65:677). Some studies have shown that antisense oligonucleotides have less transition inhibition activity in RNase H-free systems than in systems where RNase H is present (Haeuptle et al. (1986) *Nucleic Acids Res.* 14:1427–14448; Minshull et al. (1986) *Nucleic Acids Res.* 14:6433–6451), or when the chemical modification on antisense oligonucleotide is unable to evoke RNase H activity (Maher III et al. (1988) *Nucl. Acids Res.* 16:3341–3358; Leonetti et al. (1988) *Gene* 72:323–332). In addition, it has also been shown that a 4 to 6 base pair long hybrid is sufficient to evoke RNase H activity.

A 39mer RNA target sequence (SEQ ID NO:22) which encodes a portion of the HIV-1 gag gene (TABLE 1) was synthesized to study the RNase H activation property of modified cooperative oligonucleotides of the invention. As per the design, modified oligonucleotides 1, 10, and 17 bind to a 9 base site on the 3'-side of the binding site of the target, and modified oligonucleotides 2, 13, and 14 bind on the 5'-side of the target adjacent to the binding site of the former oligonucleotide. Oligonucleotide 5 binds to the entire length of the 21 bases on the target. Oligonucleotides 6, 7, 18 and 19 contained mismatches.

Figure 4A:
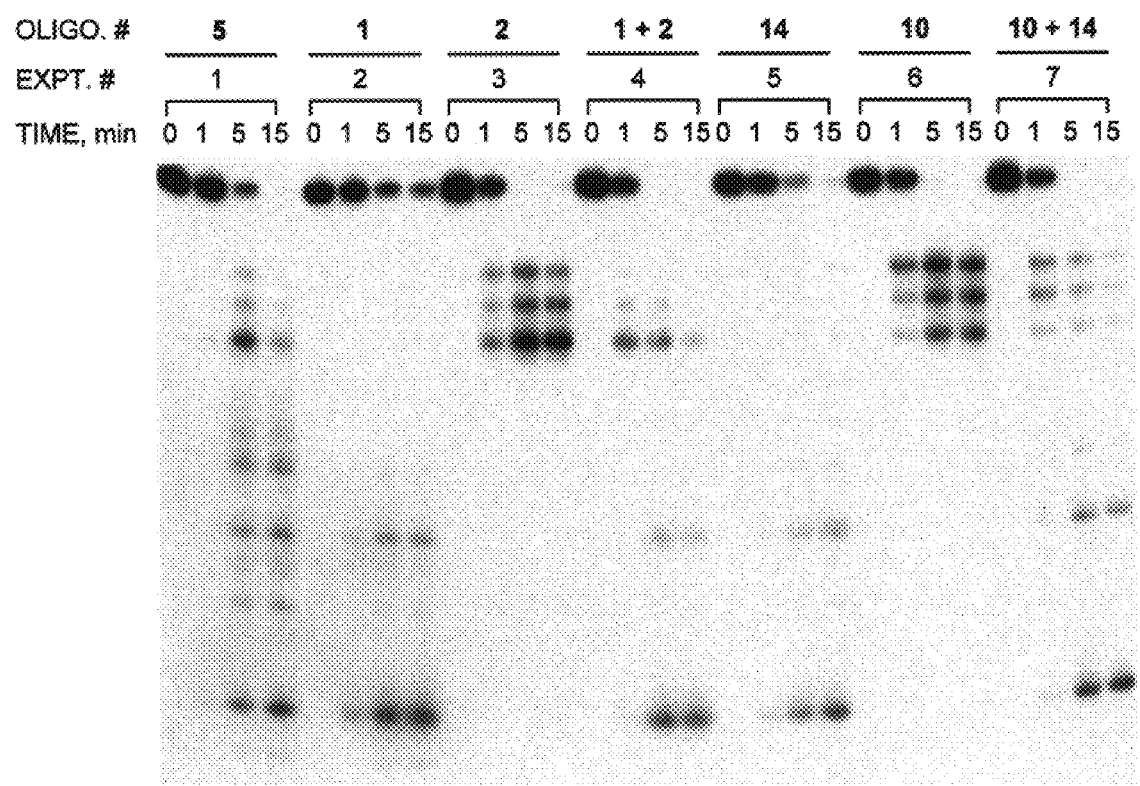
FIG. 4A is an autoradiogram showing the RNase H hydrolysis pattern of the RNA target sequence in the presence of oligonucleotides 5, 1, 2, 1+2, 14, 10, and 10+14 at different time points.
Figure 4B:
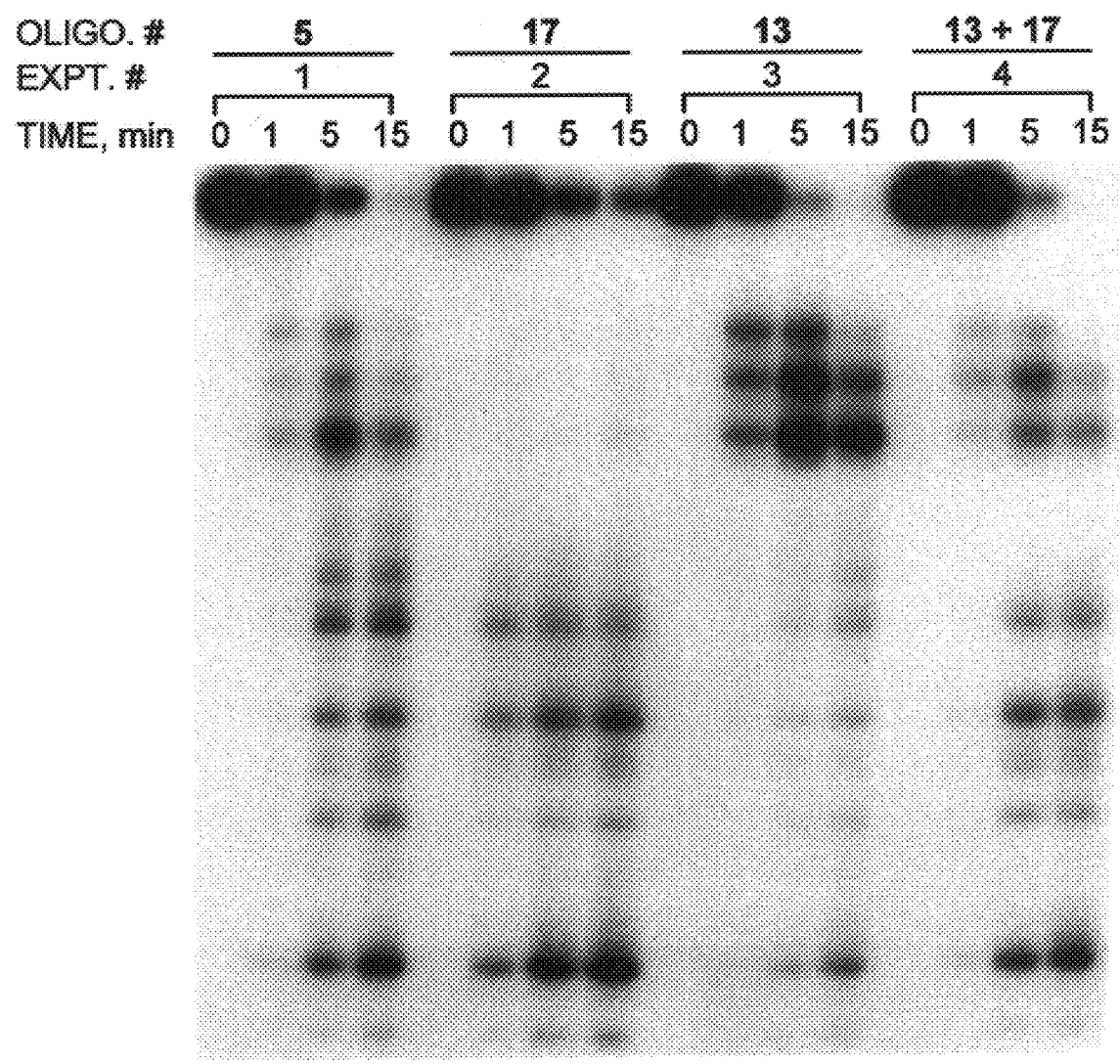
FIG. 4B is an autoradiogram showing the RNase H hydrolysis pattern of the RNA target sequence in the presence of oligonucleotides 5, 13, 17, and 13+17 at different time points.

An autoradiogram showing the RNase H hydrolysis pattern of the RNA target in the absence and presence of oligonucleotides of the invention is shown in FIGS. 4A and 4B. As expected, in experiments 2 and 5 (FIG. 4A), and in experiment 2 (FIG. 4B), hydrolytic activity is observed towards the 3'-end of the target RNA (lower half of the autoradiogram) in which oligonucleotides 1, 14, and 17, respectively, are present. Similarly, in experiments 3 and 6 (FIG. 4A) and in experiment 3 (FIG. 4B), RNA degradation bands are present only in the upper half of the autoradiogram, indicating the binding of oligonucleotides 2, 10, and 13, respectively, on the 5'-side of the target. When combinations of oligonucleotides are present (i.e., 1+2, 10+14, and 13+17) in experiments 4 and 7 (FIG. 4A) and in experiment 4 (FIG. 4B), the RNase H degradation pattern obtained is very similar to the one observed in the case of control oligonucleotide 5 in experiment 1 (FIGS. 5A and 5B). This clearly indicates that the new short tandem cooperative oligonucleotides of the invention bind to the target RNA as expected with sequence specificity and evoke RNase H activity.

Figure 5:
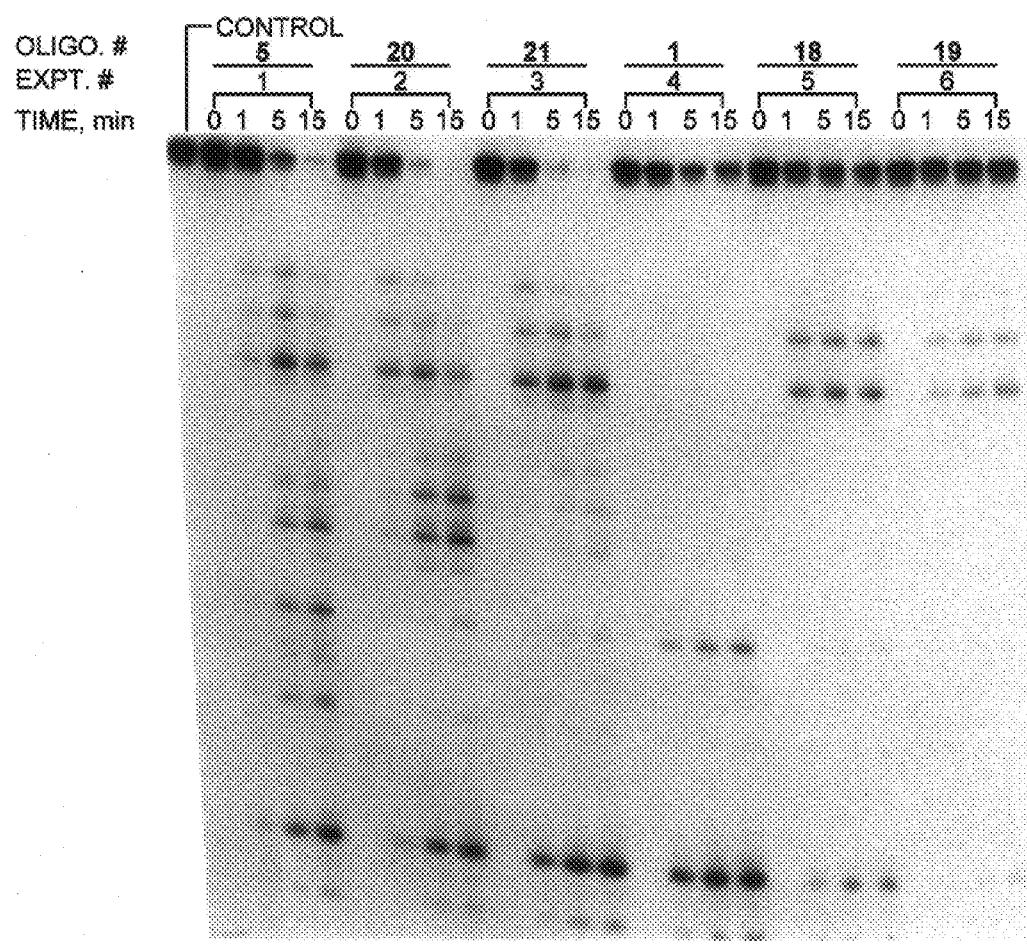
FIG. 5 is an autoradiogram showing the RNase H hydrolysis pattern of RNA target in the presence of the mismatched oligonucleotides 23, 24, 18 and 19 compared to the control matched oligonucleotide 5 and 1 at different time points.

To further understand sequence specificity of the cooperative oligonucleotides versus longer oligonucleotides, two short oligonucleotides analogous to oligonucleotide 1 having one and two mismatches, oligonucleotides 18 (SEQ ID NO:18) and 19 (SEQ ID NO:19), were synthesized and studied for RNase H activation in comparison to oligonucleotides 23 and 24. FIG. 5 shows the RNase H hydrolytic pattern of target RNA in the presence of the mismatched oligonucleotides. Oligonucleotide 23 (SEQ ID NO:23) with 1 mismatch (experiment 2) shows the same RNase H degradation pattern as completely matched oligonucleotide 5 (experiment 1). Oligonucleotide 24 (SEQ ID NO:24) with two mismatches (experiment 3) shows little or no RNA hydrolysis in the middle of the binding site, where the mismatches are located. However, on either side of the mismatches the degradation pattern is exactly like that found with oligonucleotide 5 which has no mismatches. This clearly indicates that, in spite of the two mismatches, oligonucleotide 24 binds to the target strongly 14 enough to activate RNase H. Oligonucleotide 18 with one mismatch (experiment 5) shows little or no RNA degradation compared to oligonucleotide 1 (experiment 4). However, it appears that oligonucleotide 18 has a strong binding site on the 5'-end of the RNA target as indicated by the RNA degradation bands towards the 5'-end of the RNA. No digestion of the 3'-end of the RNA target and little digestion of the 5'-end was observed with oligonucleotide 19, which has two mismatches (experiment 6). This clearly demonstrates that the new cooperative oligonucleotides bind with sequence specificity.

Figure 6:
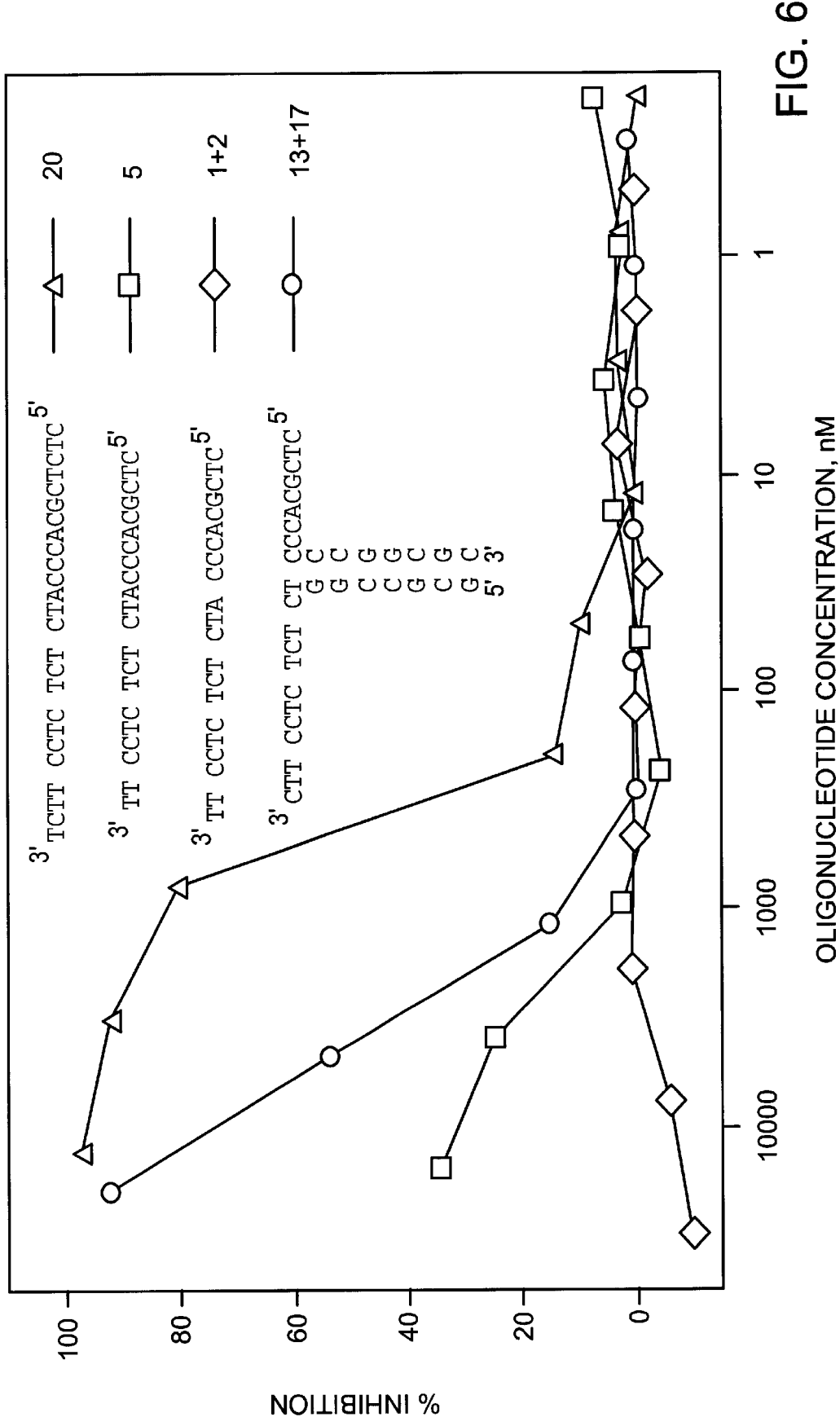
FIG. 6 is a graphic representation showing the ability of cooperative oligonucleotide oligonucleotides 1+2 (--◊--), and 13+17 (--○--), and control oligonucleotides 5 (--□--) and 20 (--∆--) at varying concentrations to inhibit HIV-1 in a cell culture system.
Figure 7:
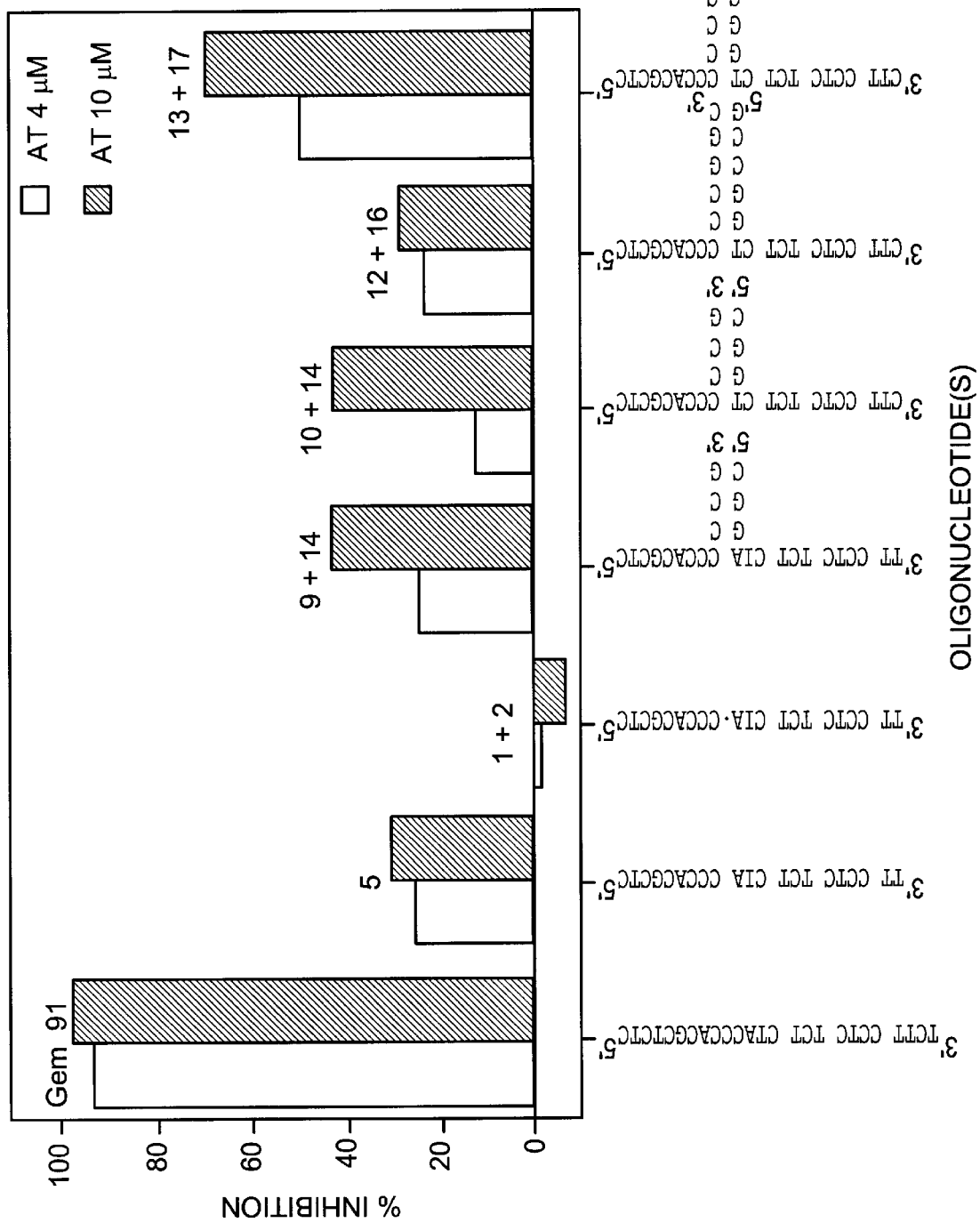
FIG. 7 is a graphic representation showing the percent inhibition of HIV-1 in cell cultures by cooperative antisense oligonucleotides 1+2, 13+17, 9+14, 10+14, and 12+16 and by control antisense oligonucleotides 5 and 20, present at two different concentrations.

Representative modified cooperative oligonucleotides of the invention were also studied for their HIV-1 virus inhibition properties in cell cultures. The results using phosphorothioate cooperative oligonucleotides are shown in FIG. 6 as a graph of percent virus inhibition versus concentration of the oligonucleotide(s) and FIG. 7. oligonucleotide 5, a 21mer that is 4 bases shorter than oligonucleotide 20, demonstrated little or no significant activity up to a 15 $\mu$M concentration. Similarly, the combination of oligonucleotides 1+2, which bind to the same sequence on the target as oligonucleotide 5, also failed to show much activity. The $IC_{50}$ for oligonucleotide 20 in the same assay system was about 0.55 $\mu$M. In contrast, a pronounced synergistic effect is observed with oligonucleotide combination 13+17 which forms a 7 base pair dimerization duplex stem. This oligonucleotide combination showed activity close to oligonucleotide 20, with an $IC_{50}$ value of about 4.0 $\mu$M. The combination 10+4, which forms a three base pair extended dimerization stem, showed about 15% virus inhibition at 4 $\mu$M concentration (FIG. 7). Combination 12+16, with a five base extended dimerization domain, showed about 25% viral inhibition at the same concentration (FIG. 7). Thus, the inhibition of HIV-1 virus progression by combinations of oligonucleotides is higher than the average of either oligonucleotide of the pair tested alone. Note that the concentration of each oligonucleotide in a combination is half that of the individual oligonucleotide tested alone. For example, the concentration of oligonucleotides 13 and 17 is 2 plus 2, to a total concentration of 4 $\mu$M, whereas the concentration of oligonucleotide 17, when it was tested alone, was 4 $\mu$M. The other oligonucleotides studied individually or in combinations did not show significant activity even up to 10 $\mu$M concentration (FIG. 7). The oligonucleotides 9+14, which form a 3 base pair duplex stem without a base separation between the binding oligonucleotides on the target, showed comparable activity to that of the combination of oligonucleotides 12 and 16, which form a 5 base pair duplex stem but with a one base separation. This result correlates well with the Tm data (Table 3).

Figure 8:
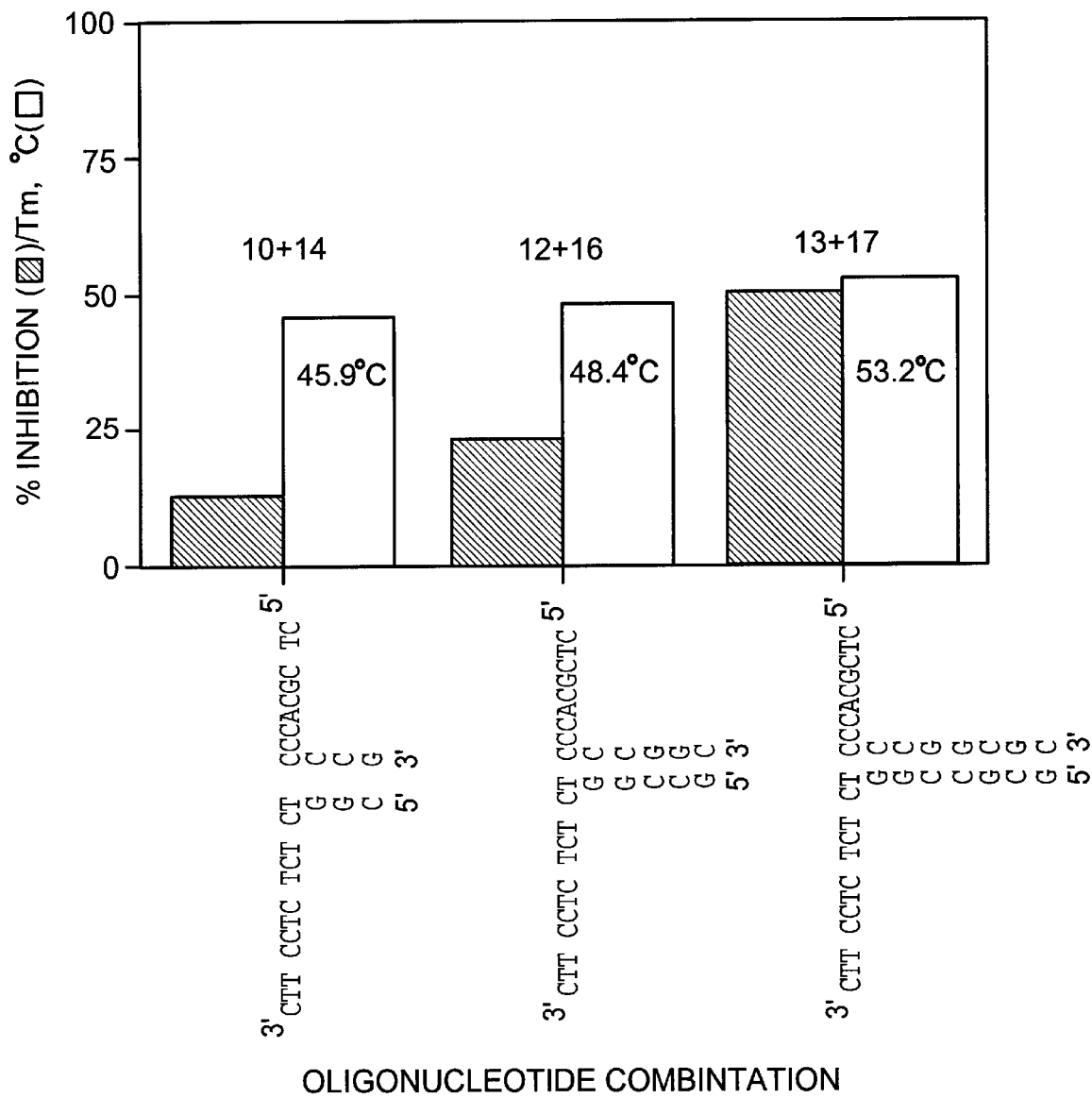
FIG. 8 is a graphic representation showing the relationship between melting temperature (Tm) and percent HIV-1 inhibition for cooperative oligonucleotides 10+14, 12+16, and 13+17.

The oligonucleotide combinations with an extended dimerization domain inhibited HIV much more efficiently than oligonucleotide 5 or the combination of oligonucleotides 1 and 2. FIG. 8 shows the relationship between HIV-1 inhibition and Tm of the complex formed. The oligonucleotide combination 13 and 17, which forms a 7 base pair antisense duplex stem, showed significantly greater activity relative to the other combinations of oligonucleotides, which form 3, 4, and 5 base pair duplex stems and oligonucleotide 5, a 21-mer.

These results demonstrate that modified cooperative oligonucleotides with dimerization domains have an enhanced ability to inhibit the expression of the target gene.

Sequence specific and cooperative binding of short oligonucleotides that bind to adjacent sites are useful to target sequences with point mutations specifically. In addition, undesirable non-sequence specific effects can be reduced by using two short oligonucleotides that can bind to a longer target sequence rather than one long oligonucleotide that binds to the same length of the target sequence. For example, long oligonucleotides that contain a modified backbone, such as phosphorothioates, activate complement, which have adverse cardiovascular effects (Galbraith et al. (1994) *Antisense Res. Dev.* 4:201–207; and Cornish et al. (1993) *Pharmacol. Commun.* 3:239–247). In conclusion, combination oligonucleotides represent an alternative therapeutic strategy to the use of a single oligonucleotide, in cases in which use of the latter is limited by concentration and chain length constraints, and the associated problems of toxicity and production costs.

The synthetic cooperative oligonucleotides of the invention also may be used to identify the presence of the nucleic acids of a particular virion or bacteria in cell cultures, for example, by labelling the oligonucleotide and screening for double-stranded, labelled DNA in the cells by in situ hybridization or some other art-recognized detection method.

In addition, the function of various genes in an animal, including those essential to animal development can be examined using the cooperative oligonucleotides of the invention. Presently, gene function can only be examined by the arduous task of making a "knock out" animal such as a mouse. This task is difficult, time-consuming and cannot be accomplished for genes essential to animal development since the "knock out" would produce a lethal phenotype. The present invention overcomes the shortcomings of this model.

It is known that antisense oligonucleotides can bind to a target single-stranded nucleic acid molecule according to the Watson-Crick or the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H if a contiguous region of deoxyribonucleotides exists in the oligonucleotide, and/or by destroying the target via reactive groups attached directly to the antisense oligonucleotide.

Thus, because of the properties described above, such oligonucleotides are useful therapeutically by their ability to control or down-regulate the expression of a particular gene in a cell, e.g., in a cell culture or in an animal, according to the method of the present invention.

The cooperative oligonucleotides of the invention may also be used to inhibit transcription of any gene in a cell, including a foreign gene. For example, the cooperative oligonucleotides as provided by the invention may be use to inhibit the expression of HIV genes within infected host cells and thus to inhibit production of HIV virions by those cells. The synthetic oligonucleotides of the invention are thus useful for treatment of HIV infection and AIDS in mammals, particularly the treatment of mammals used as animal models to study HIV infection and AIDS. The synthetic oligonucleotides of the invention are also useful for treatment of humans infected with HIV and those suffering from AIDS.

As discussed above, the synthetic oligonucleotides of the invention may be used as a pharmaceutical composition when combined with a pharmaceutically acceptable carrier. The term "pharmaceutically acceptable" means a non-toxic material that does not interfere with the effectiveness of the biological activity of the active ingredient(s). The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of virus or bacterial production by infected cells. For example, combinations of synthetic oligonucleotides, each of which inhibits transcription of a different HIV gene, may be used in the pharmaceutical compositions of the invention. The pharmaceutical composition of the invention may further contain nucleotide analogs such as azidothymidine, dideoxycytidine, dideotyinosine, and the like. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-HIV factor and/or agent to minimize side effects of the anti-HIV factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323.

The pharmaceutical composition of the invention may further include compounds which enhance delivery of oligonucleotides into cells, as described in commonly assigned U.S. patent application Ser. Nos. 08/252,072 and 08/341,522.

As used herein, the term "therapeutically effective amount" means the total amount of each active component of the pharmaceutical composition or method that is sufficient to show a meaningful patient benefit, e.g., healing of chronic conditions characterized by HIV and associated infections and complications or by other viral infections or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotide of the invention is administered to a mammal infected with HIV. The synthetic oligonucleotide of the invention may be administered in accordance with the method of the invention either alone or in combination with other therapies such as treatments employing cytokines, lymphokines, other hematopoietic factors, other anti-viral agents, and the like. When co-administered with one or more cytokines, lymphokines or other hematopoietic factors, other anti-viral agents, the synthetic oligonucleotide of the invention may be administered either simultaneously with the cytokine(s), lymphokine(s), other hematopoietic factor(s), other antiviral agents, and the like, or sequentially. If administered sequentially, the attending physician will decide on the appropriate sequence of administering the synthetic oligonucleotide of the invention in combination with cytokine(s), lymphokine(s), other hematopoietic factor(s), anti-viral agents, and the like.

Administration of the synthetic oligonucleotide of the invention used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, cutaneous or subcutaneous injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 1 ng to about 100 mg of synthetic oligonucleotide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the synthetic oligonucleotide will be in the range of 12 to 24 hours of continuous intravenous administration. Ultimately, the attending physician will decide on the appropriate duration of intravenous therapy using the pharmaceutical composition of the present invention.

The following examples illustrate the preferred modes of making and practicing the present invention, but are not meant to limit the scope of the invention since alternative methods may be utilized to obtain similar results.

EXAMPLES

1. Cooperative Oligonucleotide Synthesis

Cooperative oligodeoxyribonucleotides were synthesized on a Milligen 8700 DNA synthesizer using β-cyanoethylphosphoramidite chemistry (*Meth. Mol. Biol.* (1993) Vol. 20 (Agrawal (ed.) Humana Press, Totowa, N.J., pp. 33–61) on a (500 Å controlled pore glass solid support). Monomer synthons and other DNA synthesis reagents were obtained from Milligen Biosearch (Burlington, Mass.). After the synthesis and deprotection, oligonucleotides were purified on reverse phase ($C_{18}$) HPLC, detritylated, desalted (Waters $C_{18}$ sep-pack cartridges (Waters, Milford, Mass.), and checked for purity by polyacrylamide gel electrophoresis (Manniatis et al. in *Molecular Cloning (A Laboratory Manual)*, Cold Spring Harbor Laboratory, Cold Spring Harbor, N.Y.). Cooperative oligoribonucleotides and hybrids (RNA/DNA) cooperative oligonucleotides are prepared according to the method(s) of Metelev et al. (*FEBS. Lett.* (1988) 226:232–234; and Atabekov et al. (1988) *FEBS. Lett.* 232:96–98.

Cooperative phosphorothioate oligonucleotides for RNase H and tissue culture experiments were synthesized as above but using sulfurizing agent as oxidant instead of normal iodine oxidant. Post-synthetic processing was carried out exactly as above but desalting was performed by dialysis for 72 hours against double distilled water.

Other modified forms of the cooperative oligonucleotides are prepared as described in Agrawal (ed.) (*Meth. Mol. Biol.*, Vol. 20, *Protocols for Oligonucleotides and Analogs*, (1993) Humana Press, Totowa, N.J.).

2. UV Melting Studies

UV melting experiments were carried out in 150 mM sodium chloride, 10 mM sodium dihydrogen phosphate, and 2 mM magnesium chloride, pH 7.4 buffer. The oligonucleotide concentration was 0.36 μM as single strand. The oligonucleotides were mixed in buffer, heated to 95° C., cooled down to room temperature, and left at 4° C. overnight. Thermal denaturation profiles were recorded at 260 nm at a heating rate of 0.5° C./min on a spectrophotometer (Perkin-Elmer Lamba2, (Norwalk Conn.) equipped with a peltier thermal controller and attached to a personal computer for data collection. The (Tm) melting temperatures were measured from first derivative plots (dA/dT vs T). Each value is an average of two separate runs and the values are within ±1.0° C. range.

3. RNase H Assay

An RNA target (SEQ ID NO:22) was labelled at its 3'-end using terminal transferase and [α-$^{32}$P] ddATP (Amersham, (Arlington Heights, Ill.) using standard protocols (Manniatis et al. in *Molecular Cloning, A Laboratory Manual*, Cold Spring Harbor Laboratory, Cold Spring Harbor, N.Y.). End-labelled RNA (3000–5000 cpm) was incubated with 1 to 1.5 ratio of the oligonucleotides in 30 μl of 20 mM Tris-HCl, pH 7.5, 10 mM $MgCl_2$, 10 mM KCl, 0.1 mM DTT, 5% sucrose (w/v), and 40 units of RNasin (Promega, Madison, Wis.) at 4° C. overnight. An aliquot (7 μl) was taken out as control, 1 μl (0.8 unit) of *E. coli* RNase H (Promega, Madison, Wis.) was added to the remaining reaction mixture and incubated at room temperature. Aliquots (7 μl) were taken out at different time intervals. The samples were then analyzed on a 7 M urea 20% polyacrylamide gel. After the electrophoresis, an autoradiogram was developed by exposing the gel to Kodak X-Omat AR film at −70° C.

4. Antiviral Assay

The effect of the antisense oligonucleotides on the replication of HIV-1 during an acute infection was determined. The test system is a modification of the standard cytopathic effect (CPE)-based MT-2 cell assay (Posner et al. (1991) *J. Immunol.* 146:4325; Pawels et al. (1988) *J. Virol. Methods* 20:309; Mosmann (1983) *J. Immunol. Methods* 65:55). Briefly, serial dilutions of antisense oligonucleotides synthesized as described above, or the combinations of such oligonucleotides, were prepared in 50 µM L-glutamine, 100 µU/ml penicillin, 100 µg/ml streptomycin), in triplicate, in 96-well plates. Virus, (HIV-1 IIIB originally obtained from Dr. Robert Gallo, NCI (Popovic et al. (1984) *Science* 224:497) and propagated in H9 cells (Gazdar et al. (1980) *Blood* 55:409) by the method of Vujcic (*J. Infect. Dis.* (1988) 157:1047), diluted to contain a 90% cytopathic effect (CPE) dose of virus in 50 µl, was added followed by 100 µl of 4×10$^5$/ml MT-2 cells (Harada et al. (1985) *Science* 229:563) in complete medium. The plates were incubated at 37° C. in 5% $CO_2$, for 5 days. 3-[4,5-dimethylthiazol-2-yl]-2, 5-diphenyltetrazolium bromide; thiazoyl blue (MTT) dye (Sigma, St. Louis, Mo.) was added and quantitated at $OD_{540}$-$OD_{690}$ as described (Posner et al. (1991) *J. Immunol.* 146:4325). Percent viral inhibition was calculated by the formula:

(experimental−virus control)/(medium control−virus control)×100.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A composition comprising at least two synthetic cooperative oligonucleotides, wherein each oligonucleotide comprises a region complementary to a tandem, non-overlapping region of a target nucleic acid, and a dimerization domain at a terminus of each oligonucleotide, the tandem, non-overlapping regions of the target nucleic acid being separated by 0 to 1 base, the dimerization domains of the oligonucleotides being complementary to each other, and the target nucleic acid being an mRNA, a single-stranded viral DNA, or a single-stranded viral RNA.

2. The composition of claim 1, wherein each of the oligonucleotides are about 9–25 nucleotides in length.

3. The composition of claim 1, wherein the dimerization domain of a first cooperative oligonucleotide is located at the 3' terminal portion of said first oligonucleotide, and is complementary to the dimerization domain of a second oligonucleotide which is located at the 5' terminal portion of said second oligonucleotide.

4. The composition of claim 1, wherein the dimerization domain of each of the oligonucleotides is 3 to 7 nucleotides in length.

5. The composition of claim 1, wherein at least one of the oligonucleotides is modified.

6. The composition of claim 5, wherein at least one of the oligonucleotides contains at least one non-phosphodiester internucleotide linkage.

7. The composition of claim 5, wherein at least one of the oligonucleotides contains at least one phosphorothioate internucleotide linkage.

8. A duplex structure comprising a first and second synthetic cooperative oligonucleotide, wherein each oligonucleotide comprises a region complementary to a tandem, non-overlapping region of a target nucleic acid, the tandem, non-overlapping regions of the target nucleic acid being separated by 0–1 base, the target nucleic acid being an mRNA, a single-stranded viral DNA, or a single-stranded viral RNA, and the first oligonucleotide having a terminal dimerization domain complementary and hybridized to the dimerization domain of the second oligonucleotide when the first and second oligonucleotides are hybridized to the target nucleic acid.

9. The duplex structure of claim 8, wherein each of the oligonucleotides are about 9 to 25 nucleotides in length.

10. The duplex structure of claim 8, wherein the dimerization domains of the first and second oligonucleotides each comprise about 3 to 7 nucleotides.

11. A method of inhibiting the expression of a nucleic acid in vitro comprising the step of treating the nucleic acid with the pharmaceutical formulation of claim 1.

12. A method of inhibiting the expression of a nucleic acid in vitro comprising the step of treating the nucleic acid with the composition of claim 8.

13. The method of claim 11 wherein the first and second oligonucleotides are complementary to an HIV DNA and/or HIV RNA.

14. A ternary structure comprising the duplex structure of claim 8 and a target oligonucleotide to which regions of the first and second cooperative oligonucleotides are complementary.

15. A composition comprising at least a first synthetic cooperative oligonucleotide and a second synthetic cooperative oligonucleotide, wherein each oligonucleotide comprises a region complementary to one of tandem, non-overlapping regions of a target nucleic acid, and a dimerization domain consisting of 3 to 7 nucleotides at a terminus of each of the oligonucleotides, the dimerization domains of the oligonucleotides being complementary to each other, and the target nucleic acid being an MRNA, a single-stranded viral DNA, or a single-stranded viral RNA.

16. The composition of claim 15, wherein the oligonucleotides are complementary to tandem regions of the target nucleic acid that are separated by 0 to 3 bases.

17. The composition of claim 15, wherein each of the oligonucleotides is about 9 to 25 nucleotides in length.

18. The composition of claim 15, wherein the dimerization domain of the first cooperative oligonucleotide is located at the 3' terminal portion of said first oligonucleotide, and is complementary to the dimerization domain of the second oligonucleotide which is located at the 5' terminal portion of said second oligonucleotide.

19. The composition of claim 15, wherein the complementary region and the dimerization domain of each of said oligonucleotide is separated by 0 to 3 bases.

20. The composition of claim 15, wherein at least one of the oligonucleotides is modified.

21. The composition of claim 20, wherein at least one of the oligonucleotides contains at least one non-phosphodiester internucleotide linkage.

22. The composition of claim 20, wherein at least one of the oligonucleotides contains at least one phosphorothioate internucleotide linkage.

* * * * *

UNITED STATES PATENT AND TRADEMARK OFFICE
CERTIFICATE OF CORRECTION

PATENT NO. : 6,372,427 B1
DATED : April 16, 2002
INVENTOR(S) : Kandimalla et al.

It is certified that error appears in the above-identified patent and that said Letters Patent is hereby corrected as shown below:

Column 30,
Line 16, please delete the phrase "pharmaceutical formulation" and insert in its place the word -- composition --.
Line 30, please delete the phrase "one of" and replace it with the word -- a --.
Line 31, please delete the word "regions" and replace it with the word -- region --.

Signed and Sealed this

First Day of October, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 9 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:1:

CTCGCACCC    9

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

ATCTCTCTCC TT    12

(2) INFORMATION FOR SEQ ID NO:3:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

TCTCTCTCCT TC                                                    12

(2) INFORMATION FOR SEQ ID NO:4:

(i) SEQUENCE CHARACTERISTICS:
             (A) LENGTH: 12 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

CTCTCTCCTT CT                                                    12

(2) INFORMATION FOR SEQ ID NO:5:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

CTCGCACCCA TCTCTCTCCT T                                          21

(2) INFORMATION FOR SEQ ID NO:6:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

CTCGCACCCG TCTCTCTCCT TC                                         22

(2) INFORMATION FOR SEQ ID NO:7:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:7:

CTCGCACCCG CCTCTCTCCT TCT                                    23

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

ATCTCTCTCC TTC                                               13

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

CGGATCTCTC TCCTT                                             15

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

CGGTCTCTCT CCTTC                                             15

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:11:

CCGGTCTCTC TCCTTC                                            16

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:12:

```
GCCGGTCTCT CTCCTTC                                            17
```

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:13:

```
GCGCCGGTCT CTCTCCTTC                                          19
```

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:14:

```
CTCGCACCCC CG                                                 12
```

(2) INFORMATION FOR SEQ ID NO:15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:15:

```
CTCGCACCCC CGG                                                13
```

(2) INFORMATION FOR SEQ ID NO:16:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:16:

CTCGCACCCC CGGC                                                        14

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:17:

CTCGCACCCC CGGCGC                                                      16

(2) INFORMATION FOR SEQ ID NO:18:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:18:

CTCTCACCC                                                               9

(2) INFORMATION FOR SEQ ID NO:19:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:19:

CTCTCAACC                                                               9

(2) INFORMATION FOR SEQ ID NO:20:

(i) SEQUENCE CHARACTERISTICS:
        (A) LENGTH: 25 base pairs
        (B) TYPE: nucleic acid (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:20:

CTCTCGCACC CATCTCTCTC CTTCT                                                  25

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

CTAGAAGGAG AGAGATGGGT GCGAGAG                                                27

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (xi) SEQUENCE DESCRIPTION: SEQ ID NO:22:

AGAAGGAGAG AGAUGGGUGC GAGAGCGUCA GUAUUAAGC                                   39

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:23:

CTCTCACCCA TCTCTCTCCT T                                                      21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued

```
    (ii)  MOLECULE TYPE: cDNA (iii) HYPOTHETICAL: YES (iv)  ANTI-SENSE: YES (xi)  SEQUENCE DESCRIPTION: SEQ ID NO:24:

CTCTCAACCA TCTCTCTCCT T                                                   21
```